United States Patent [19]

Cady et al.

[11] Patent Number: 5,137,874

[45] Date of Patent: Aug. 11, 1992

[54] PARTIALLY COATED $C_{10}$–$C_{20}$ FATTY ACID SALTS OF PEPTIDES HAVING MOLECULAR WEIGHTS UP TO ABOUT 5,000

[75] Inventors: Susan M. Cady, Yardley, Pa.; Richard Fishbein, Skillman, N.J.

[73] Assignee: American Cyanamid Co., Stamford, Conn.

[21] Appl. No.: 661,787

[22] Filed: Feb. 25, 1991

Related U.S. Application Data

[63] Continuation-in-part of Ser. No. 376,181, Jul. 5, 1989, abandoned, which is a continuation of Ser. No. 181,795, Apr. 15, 1988, abandoned, which is a continuation-in-part of Ser. No. 759,701, Jul. 29, 1985, abandoned.

[51] Int. Cl.$^5$ .................. A61K 37/00; A01N 37/18; A01N 37/12; A61F 13/00
[52] U.S. Cl. .......................... 514/17; 514/2; 514/547; 424/422; 424/468
[58] Field of Search .............. 514/2, 547, 17; 424/422, 468

[56] References Cited

U.S. PATENT DOCUMENTS

| | | | |
|---|---|---|---|
| 2,517,513 | 8/1950 | Vaernet | 128/271 |
| 3,857,932 | 12/1974 | Shepherd et al. | 424/19 |
| 4,256,737 | 3/1981 | Nestor | 424/177 |
| 4,411,890 | 10/1983 | Momany | 424/177 |
| 4,450,150 | 5/1984 | Sidman | 424/1.1 |
| 4,604,376 | 8/1986 | Teng | 514/3 |
| 4,786,501 | 11/1988 | Janski et al. | 424/422 |
| 4,985,404 | 1/1991 | Mitchell | 514/6 |

FOREIGN PATENT DOCUMENTS

| | | |
|---|---|---|
| 55983/86 | 4/1986 | Australia . |
| 0013949 | 8/1980 | European Pat. Off. . |
| 0052510 | 5/1982 | European Pat. Off. . |
| 0058481 | 8/1982 | European Pat. Off. . |
| 0133988 | 3/1985 | European Pat. Off. . |
| 0158277 | 10/1985 | European Pat. Off. . |

OTHER PUBLICATIONS

Hackh's Chemical Dictionary, 4th Ed., McGraw-Hill Book Co., p. 497.
Remington's Pharmaceutical Sciences, 15th Ed. 1975, Mack Pub. Co., pp. 1618–1635.

*Primary Examiner*—Frederick E. Waddell
*Assistant Examiner*—Gregory Hook
*Attorney, Agent, or Firm*—Alice C. Brennan

[57] ABSTRACT

The invention relates to compositions for the parenteral administration of an essentially uniform and continuous amount of a peptide, which has a molecular weight of up to about 5,000, over an extended period of time. The peptide composition comprises a compacted and partially coated $C_{10}$–$C_{20}$ fatty acid salt of the peptide. Examples of peptides useful in the invention include his-D-trp-ala-trp-D-phe-lys-$NH_2$, bradykinin, luteinizing hormone releasing hormone, growth releasing factor and poly-l-lysine. The invention also relates to the preparation and administration of said peptide compositions.

12 Claims, 3 Drawing Sheets

PARTIALLY COATED C$_{10}$–C$_{20}$ FATTY ACID SALTS OF PEPTIDES HAVING MOLECULAR WEIGHTS UP TO ABOUT 5,000

This is a continuation-in-part a Ser. No. 07/376,181, filed Jul. 5, 1989, abandoned, which is a continuation of application Ser. No. 07/181,795, filed Apr. 15, 1988, abandoned, which is a continuation-in-part of application Ser. No. 06/759,701, filed Jul. 29, 1985, abandoned.

BACKGROUND OF THE INVENTION

The difficulties encountered in the development of methods and compositions which continuously release pharmaceutical preparations in a uniform manner over extended periods of time are well known (see, for example, Remington's Pharmaceutical Sciences, 15th Edition, (1975), pages 1618–1635).

Recent developments in the area of controlling the release of drugs are disclosed in European Patent Application 81305426.9 and European Patent Application 82300416.3 which describe methods for controlling the release of drugs by microencapsulation and containment within a biodegradable matrix, respectively.

SUMMARY OF THE INVENTION

The present invention provides a novel composition for the parenteral administration of an essentially uniform and continuous amount of a peptide over an extended period of time comprising a compacted and partially coated fatty acid salt of a peptide, which exhibits some degree of solubility in an aqueous physiological environment. The invention is advantageous since it provides a useful method to control the dosage and/or the rate of the delivery of the peptide. The peptides may exhibit many pharmaceutical properties including growth promotion in animals.

Peptides suitable for use in the present invention, in general, have molecular weights of up to about 5,000. One peptide suitable for use in this composition is his-D-trp-ala-trp-D-phe-lys-NH$_2$.

Surprisingly, it has been found that for the partially coated implant of compacted C$_{10}$–C$_{20}$ fatty acid salts of the peptide his-D-trp-ala-trp-D-phe-lys-NH$_2$ that, in general, the dissolution rate decreases with increasing carbon content of the fatty acid used to prepare the salt, while this is not the case when the salts are uncoated.

The invention also is directed to the preparation and administration of said compositions.

PREFERRED EMBODIMENT OF THE INVENTION

Besides the peptide his-D-trp-ala-trp-D-phe-lys-NH$_2$, other representative peptides include bradykinin, luteinizing hormone releasing hormone, growth releasing factor and poly-1-lysine stearate.

The rate of release and dosage of the composition of the invention may be adjusted by the use of different fatty acid salts and coating materials. A preferred group of fatty acid salts for use in this invention include the C$_{10}$–C$_{20}$ fatty acid salts of the peptide his-D-trp-ala-trp-D-phe-lys-NH$_2$.

An advantage of the composition of the invention is that once the dissolution characteristics of the compacted and partially coated fatty acid salt of the peptide to be administered has been determined, the salt may be assayed, which provides for exact control of dosages, as the pure compacted salt is the implant. A further advantage of the composition of the invention is the linear nature of its dissolution profile.

The composition of the invention may optionally contain up to about 50% by weight of a diluent or mixture of diluents and up to about 5% by weight of a lubricant or mixture of lubricants. Suitable diluents for the invention are ethyl cellulose and castorwax. A suitable lubricant for the invention is magnesium stearate.

The term "aqueous physiological environment" means the body of a warm-blooded animal as well as such an in vitro environment which may be mimicked by aqueous liquids, such as phosphate buffered solutions at a temperature of 35° C. to 40° C.

An implant for the administration of peptide may be prepared by admixing the peptide his-D-trp-ala-trp-D-phe-lys-NH$_2$ in an organic solvent such as methanol with a sufficient amount of the desired fatty acid to provide for complete salt formation. The salt may then be isolated by removing the solvent, washing and drying. The isolated pure salt is pressed by compaction or extrusion into an implant, preferably cylindrical implant. The compacted material is coated with a biodegradable or non-biodegradable coating by conventional techniques. Prior to implantation a specified area of the coating is removed to expose the compacted salt. For example, the coating may be cut off at one or both of the ends of a cylindrical implant.

It has been shown in an in vivo steer study that the desirable dissolution characteristics of the compositions of the invention are maintained and that the release profiles for in vivo release and in vitro dissolution are comparable, demonstrating the effectiveness of the present compositions for the parenteral administration of a fatty acid salt of a peptide. In a controlled experiment, an implant of the tristearate salt of the peptide described above, released an average of 1.8% of the peptide present in the implant in vivo per day compared to 1.6% per day in vitro.

The invention is further illustrated by the following non-limiting examples.

EXAMPLE 1

Preparation of the tristearate salt of his-D-tro-ala-trp-D-phe-lys-$NH_2$

Stearic acid (1.025g, 3.6 mmol) is added to a solution of the peptide his-D-trp-ala-trp-D-phe-lys-$NH_2$ (1.0 g, 0.9 mmol) in methanol (15 mL) and the resulting solution is heated in a warm water bath for three hours. Evaporation of the methanol under reduced pressure produces a white powder product which is washed with ether (2440 mL), filtered and dried to yield 0.509 g, 74.7% of the desired tristearate salt with an elemental analysis C,67.13; H,9.23; N,9.83%. Calculated analysis for $C_{99}H_{165}N_{12}O_{15}$; C,67.43; H,9.43; N,9.53%.

EXAMPLES 2–10

Utilizing the procedure of Example 1 and substituting the appropriate $C_{10}$–$C_{20}$ fatty acid yields nine (9) tri-fatty $C_{10}$–$C_{20}$ fatty acid salts of the peptide his-D-trp-ala-trp-D-phe-lys-$NH_2$ listed in Table I below.

acid salt on a rotary tablet press using a 1/8″ diameter punch and die to give cylindrical implants.

The implants prepared above are coated with both biodegradable and non-biodegradable coatings by procedures A and B below.

Procedure A

Non-Biodegradable Silicon Polymer

Clean grade silicon elastomer (ID parts) is mixed with curing agent (one part) on a watch glass with a spatula. This is deaerated in a dessicator for 30 minutes. The implants are grasped by the ends with tweezers, rolled into the silicon polymer, placed on end on aluminum foil and cured at 40° C. for five hours. One or both of the ends are removed with a razor blade leaving the "shaft" of the cylinder coated.

Alternatively, implants may be dip coated with 20% to 40% of a medical adhesive, sold under the trademark SILASTIC® by Dow Corning, which has been dispersed in hexane, and dried and cured at 40° C. to 50° C. overnight before removing the coating from one or both of the base ends.

Procedure B

Biodegradable Coatings

The polymer or copolymer (one part) is dissolved in

TABLE I

| Fatty acid | Fatty Acid GMS | Fatty Acid mM | Peptide GMS | Peptide MM | Product GMS | Product % Yield | Molecular formula | Molecular weight | Found % C | Found % H | Found % N | Calculated % C | Calculated % H | Calculated % N |
|---|---|---|---|---|---|---|---|---|---|---|---|---|---|---|
| C10 | 0.31 | 1.8 | 0.5 | 0.458 | 0.65 | 80.7 | $C_{75}H_{117}N_{12}O_{15}$ | 1426.782 | 63.29 | 8.17 | 11.60 | 63.13 | 8.27 | 11.78 |
| C11 | 0.503 | 2.7 | 0.75 | 0.675 | 0.74 | 75.0 | $C_{78}H_{123}N_{12}O_{15}$ | 1468.86 | 63.59 | 8.35 | 11.57 | 63.78 | 8.44 | 11.44 |
| C12 | 0.72 | 3.6 | 1.0 | 0.9 | 0.9 | 67.4 | $C_{81}H_{129}N_{12}O_{15}$ | 1509.912 | 64.68 | 8.42 | 11.34 | 64.46 | 8.62 | 11.14 |
| C13 | 0.386 | 1.8 | 0.5 | 0.458 | 0.567 | 80.0 | $C_{84}H_{135}N_{12}O_{15}$ | 1551.99 | — | — | — | — | — | — |
| C14 | 0.82 | 3.6 | 1.0 | 0.9 | 0.86 | 60.0 | $C_{87}H_{141}N_{12}O_{15}$ | 1595.094 | 65.03 | 8.65 | 10.67 | 65.51 | 8.91 | 10.54 |
| C15 | 0.87 | 3.6 | 1.0 | 0.9 | 0.88 | 58.8 | $C_{90}H_{147}N_{12}O_{15}$ | 1637.172 | 65.99 | 8.74 | 10.55 | 66.02 | 9.05 | 10.27 |
| C16 | 0.92 | 3.6 | 1.0 | 0.9 | 0.86 | 57.0 | $C_{93}H_{153}N_{12}O_{15}$ | 1679.25 | 66.49 | 8.95 | 10.37 | 66.51 | 9.18 | 10.01 |
| C17 | 0.97 | 3.6 | 1.0 | 0.9 | 0.9 | 59.0 | $C_{96}H_{159}N_{12}O_{15}$ | 1721.328 | — | — | — | — | — | — |
| C20 | 1.717 | 5.49 | 1.5 | 1.37 | 1.65 | 63.2 | $C_{105}H_{177}N_{12}O_{15}$ | 1847.562 | 67.97 | 9.57 | 9.23 | 68.25 | 9.66 | 9.098 |

EXAMPLES 11–20

Preparation of the partially coated compacted implants of tri $C_{10}$–$C_{20}$ fatty acid salts of the peptide Implants are prepared weighing a sufficient quantity of the desired $C_{10}$–$C_{20}$ tri-fatty acid salt of the peptide his-D-trp-ala-trp-phe-lys-$NH_2$ to provide approximately 200 mg of the peptide as the triacetate equivalent. The salt is then compressed on a carver press at from 1000 to 5000 psig in 3/16″ diameter cylindrical die. Smaller implants (providing ~53 mg of peptide triacetate equivalents) are prepared by compressing the appropriate quantity of tri $C_{10}$–$C_{20}$ fatty chloroform (three to eight parts). Each implant is grasped by the ends with tweezers, dipped into the polymer solution, and then the chloroform evaporated at room temperature. Each implant is coated twice. After the coating dried overnight at room temperature, the polymer ends are removed with a razor blade, leaving the long cylindrical "shaft" coated.

Tables II and III below contain a summary of the physical data on the coated implants thus prepared Table II presents implant data for three (3) different coatings for nine (9) of the salts. Table III presents implant data for three (3) different coatings for four (4) of the salts.

TABLE II

| Salt | mg Peptide tri-acetate equivalents | Coating None | Coating pGLA* | Coating Silastic** | mg | mm Thick | Implant Length (mm) |
|---|---|---|---|---|---|---|---|
| C10 | 197.55 | X | — | — | — | — | 12.305 |
|  | 197.7 | — | X | — | 37.3 | 0.38 | 12.455 |
|  | 194.09 | — | — | X | 53.1 | 0.485 | 12.265 |
| C11 | 198.61 | X | — | — | — | — | 12.325 |
|  | 196.74 | — | X | — | 33.9 | 0.36 | 12.31 |
|  | 195.75 | — | — | X | 41.2 | 0.42 | 13.09 |
| C12 | 193.7 | X | — | — | — | — | 12.11 |
|  | 196.46 | — | X | — | 36.1 | 0.3755 | 12.03 |
|  | 173.98 | — | — | X | 37.8 | 0.44 | 11.05 |
| C13 | 199.8 | X | — | — | — | — | 13.4 |
|  | 166.4 | — | X | — | 17.9 | 0.045 | 11.285 |
|  | 168.9 | — | — | X | 62.0 | 0.55 | 11.475 |

TABLE II-continued

| Salt | mg Peptide tri-acetate equivalents | Coating None | Coating pGLA* | Coating Silastic** | mg | mm Thick | Implant Length (mm) |
|---|---|---|---|---|---|---|---|
| C14 | 179.71 | X | — | — | — | — | 12.4 |
|  | 198.9 | — | X | — | 19.8 | 0.0775 | 13.23 |
|  | 197.2 | — | — | X | 70.0 | 0.5325 | 13.21 |
| C15 | 190.0 | X | — | — | — | — | 14.405 |
|  | 184.0 | — | X | — | 20.7 | 0.045 | 13.45 |
|  | 189.0 | — | — | X | 68.7 | 0.585 | 13.365 |
| C16 | 196.3 | X | — | — | — | — | 14.455 |
|  | 197.6 | — | X | — | 30.8 | 0.155 | 14.18 |
|  | 203.9 | — | — | X | 82.5 | 0.4525 | 15.05 |
| C17 | 167.7 | X | — | — | — | — | 13.23 |
|  | 161.6 | — | X | — | 25.8 | 0.37 | 13.465 |
|  | 192.1 | — | — | X | 89.2 | 0.355 | 14.035 |
| C18 | 176.59 | X | — | — | — | — | 13.31 |
|  | 177.29 | — | X | — | 42.9 | 0.3975 | 13.41 |
|  | 181.09 | — | — | X | 89.4 | 0.55 | 14.11 |

*Copoly(L-lactide/glycolide) ηinh 0.32, 55/45 L-lactide/glycolide
**Silicon polymer nonbiodegradable

TABLE III

| Salt | mg Peptide tri-acetate equivalents | Coating None | Coating pGLA* | Coating Silastic** | mg | mm Thick | Implant Length (mm) |
|---|---|---|---|---|---|---|---|
| C13 | 52.74 | X | — | — | — | — | 8.225 |
|  | 47.96 | — | X | — | 7.8 | .05 | 8.39 |
|  | 48.52 | — | — | X | 24.1 | .065 | 8.145 |
| C15 | 50.98 | X | — | — | — | — | 9.0 |
|  | 50.26 | — | X | — | 6.3 | 0.04 | 10.0 |
|  | 49.6 | — | — | X | 16.3 | 0.06 | 9.25 |
| C18 | 50.28 | X | — | — | — | — | 8.33 |
|  | 51.65 | — | X | — | 3.4 | 0.0475 | 8.495 |
|  | 51.46 | — | — | X | 13.7 | 0.1225 | 9.0 |
| C20 | 50.59 | X | — | — | — | — | 10.15 |
|  | 49.18 | — | X | — | 4.8 | 0.05 | 9.37 |
|  | 51.36 | — | — | X | 15.7 | 0.07 | 10.0 |

*Copoly(L-lactide/glycolide), 55/45 L-lactide/glycolide, ηinh 0.48, S14384-52A.

EXAMPLE 21

Dissolution Experiments

Dissolution experiments are carried out at 39° C. using a shaking bottle method. Phosphate buffered saline (PBS) adjusted to pH −7.1 is the dissolution medium ($NaH_2PO_4 \cdot H_2O$ 3.46 g, $Na_2HPO_4$ 3.55 g NaCl 9.50 g dissolved in distilled Water to 1000 mL).

The implant is placed in a disposable polypropylene flat base tube (Sarstedt No 58.537 with No 67.790 cap) and 30 mL PBS is added. The tubes are placed in a 39° C. Fisher Shaking Water Bath (Model 129—shaker setting a 2¾). The PBS is changed daily and samples are assayed by optical density measurement at 210 nm to give the dissolution profiles.

Figure 1:
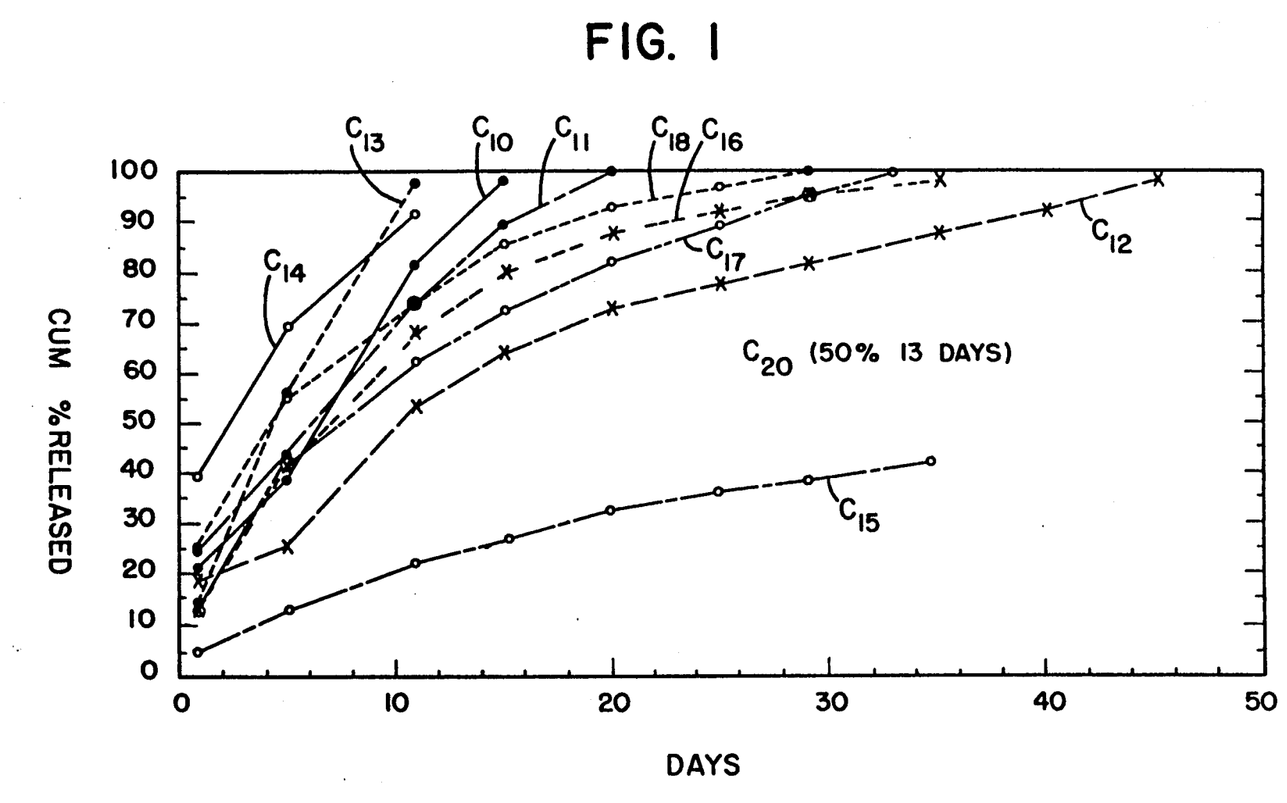
FIG. 1 is a graph of the dissolution of uncoated, compacted C$_{10}$–C$_{20}$ and fatty acid peptide salts.
Figure 2:
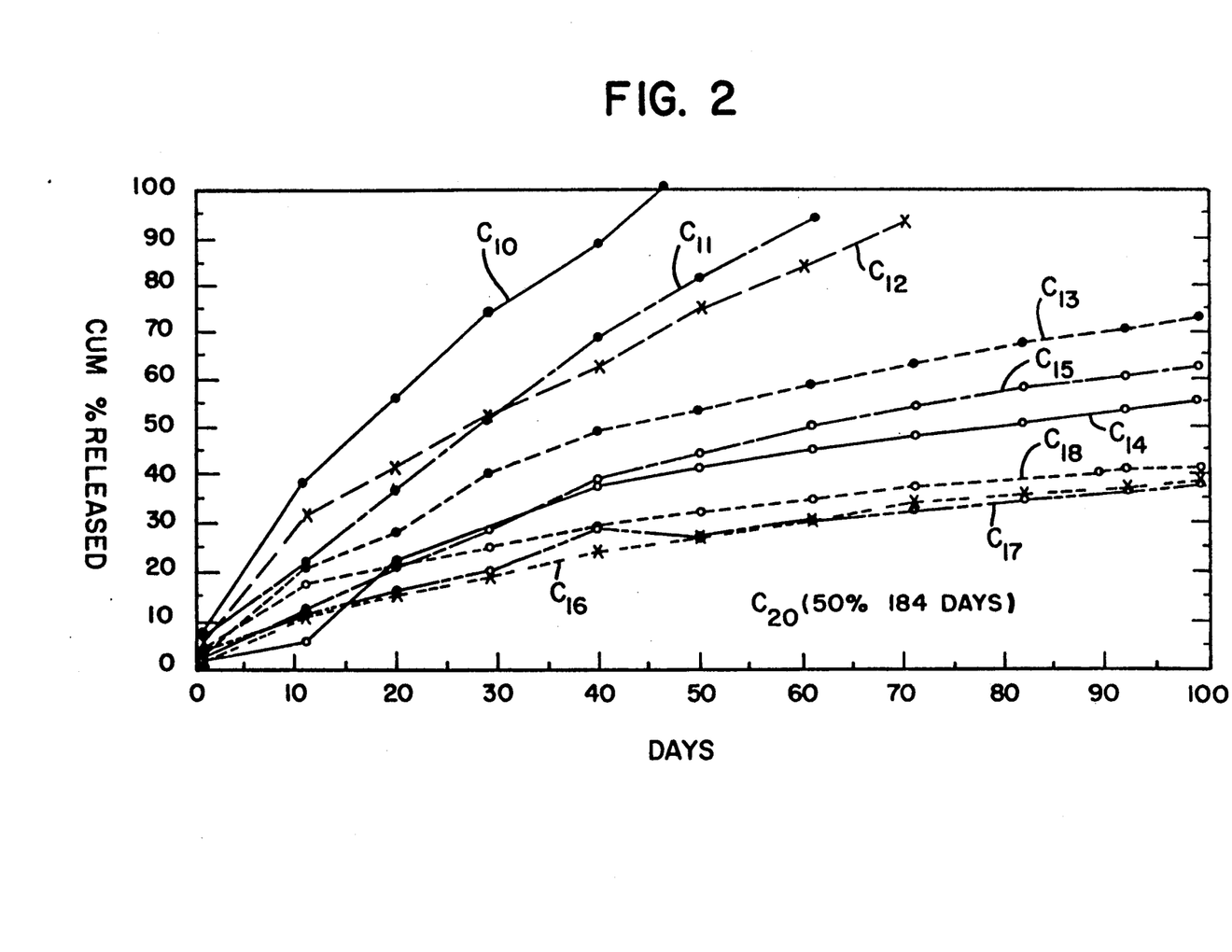
FIG. 2 is a graph of the dissolution of compacted and partially coated C$_{10}$–C$_{20}$ acid peptide salts.
Figure 3:
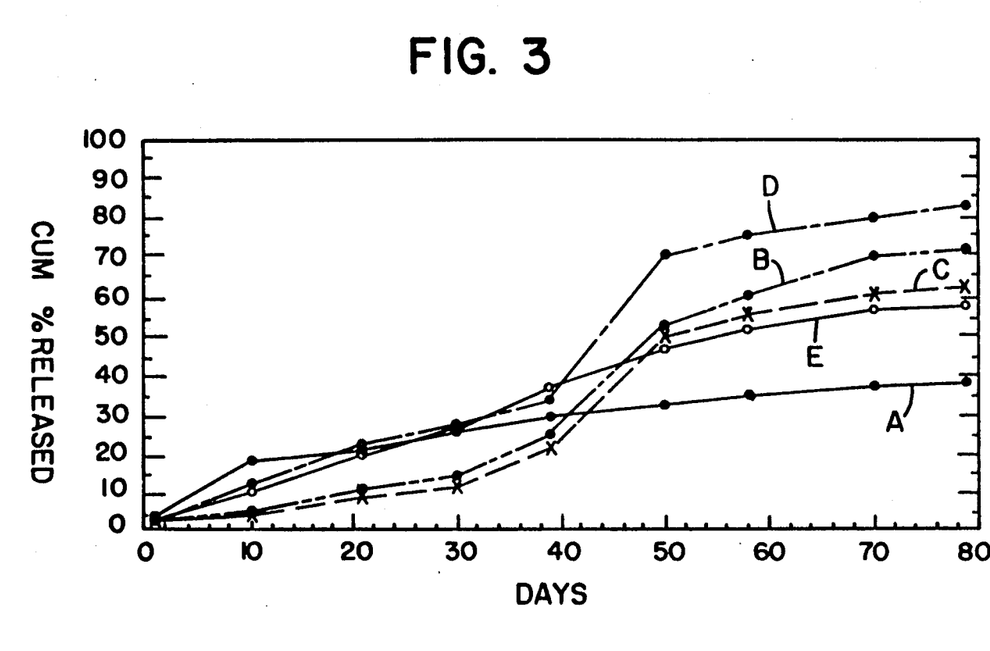
FIG. 3 is a graph showing the effect of different coatings on the dissolution profile of the tristearate salt of the peptide.

The results of these experiments are summarized in FIGS. 1, 2, and 3 below. FIG. 1 shows the dissolution of uncoated, compacted implants of $C_{10}$–$C_{20}$ fatty acid salts of the peptide his-D-trp-ala-trp-D-phe-lys-$NH_2$ in an aqueous physiological environment at 39° C. from 10 to 48 days. The dissolution kinetics and rate are altered by coating the cylindrical implant and having one or both of the ends exposed. FIG. 2 shows that complete dissolution for many of the implants has not occurred after 100 days. The use of different $C_{10}$–$C_{20}$ fatty acid salts in conjunction with various coatings on the compacted implants provides a means of regulating the release rate of the peptide over extended periods of time. FIG. 3 represents the variations in the release profiles obtained with the tristearate salt of the peptide his-D-trp-ala-trp-D-phe-lys-$NH_2$ obtained with some different biodegradable and nonbiodegradable coating materials. In FIG. 3, A is a nonbiodegradable silicon polymer; B is a biodegradable (L-lactide/glycolide, 57/43); C is biodegradable (L=lactide/glycolide, 71.6/28.4); biodegradable (poly-L-lactide) and E is biodegradable (tetramethylene carbonate/glycolide 50/50).

EXAMPLE 22

Dissolution characteristics of the partially coated complete implants of the tristearate salt of his-D-trp-ala-trp-D-phe-lys-$NH_2$ when administered to a steer (in vivo)

I. Preparation of $H^3$ labeled Peptide Tristearate salt $H^3$ labeled peptide triacetate (17.2 mg $H^3$, 0.24 mCi/mg, 0.0158 mM; and 413 mg unlabeled, 0.378 mM) are dissolved in distilled water (45 mL) in a centrifuge tube (Falcon No 2070—plastic). Ammonium hydroxide (30% $NH_3$) is added dropwise until basic (pH-10). White particles immediately precipitated after ten minutes, the tube is put into a beaker of ice water and left for 20 minutes. The tubes are centrifuged for 15 minutes (~2600 rpm, Damon-IEC Clinical Centrifuge Model CL with Model No 801 rotor). The water is decanted into another centrifuge tube and three drops ammonium hydroxide is added. After five minutes the tube is put into a beaker of ice water and left for 20 minutes. The three tubes are centrifuged as above. The water layer is decanted into a pint plastic bottle for freezing, storage and recycling. Each tube of solid centrifuge material is dissolved in methanol (15 mL) and put into one 200 mL recovery flask. Stearic acid (1.32 g, 4.72 mM) is added and the flask is put into a 600 mL beaker of warm water. This methanol solution is stirred until dissolved and then for another three hours. The product is concentrated in vacuo to give a white solid. This is washed with ether $2 \times 40$ mL), filtered, dried in a dessicator over drierite overnight yielding 662.3 mg (4.49 mCi).

II. Implant Fabrication

A Carver press (Model M, 25 ton press) is used for implant fabrication The $H^3$ labeled salts for the dissolution implants are cut with cold tristearate (1:3 hot to cold) and thoroughly mixed with a mortar pestle before compression while the animal implants are prepared directly from $H^3$ salts. Two tristearate salt implants (one for dissolution, one for animal implantation) are compressed at 5,000 psi in a custom made 3/16" die to give cylinders.

III. Implant Coating

A biodegradable polymer coating is applied by dissolving poly(glycolic acid/lactic acid) copolymer (1 g, 71.6/28.4 L-lactide/glycolide ratio, $_n$inh 0.51) in chloroform (3 mL). Each of the implants is grasped by the ends with tweezers and dipped into the polymer solution, then the chloroform is evaporated off at room temperature in a hood. Each implant is coated twice, and dried overnight at room temperature, the polymer ends are removed with a razor blade, leaving the long cylindrical "shaft" coated.

IV. Peptide Implant Administration and Behavior in vivo

Under local anesthetic, a small slit is made at the base of the ear on a 750 lb steer. A pocket is made subcutaneously and the $H^3$ labeled tristearate salt implant is inserted with forceps. The slit is sutured to prevent the implant from coming out.

The steer is maintained in a cattle metabolism cage. It is given up to ten lbs daily of Cattle Growing Ration No 632. Hay and water are provided ad libitum. The total amount of urine and feces are collected daily, volume and weight are measured and representative samples are sent for radioactivity determination. Blood samples are taken periodically to assay peptide blood levels.

Calculations of in vivo peptide release are based on the daily total amount of radioactivity appearing in the urine and feces.

V. Comparative in vitro Dissolution

Dissolution experiments are carried out at 39° C. using a shaking bottle method. Phosphate buffered saline (PBs) adjusted to pH =7.1 is the dissolution medium ($NaH_2PO_4 \cdot H_2O$ 3.45 g, $Na_2HPO_4$ 3.55 g, NaCl 9.50 g is dissolved in distilled water to 1000 mL).

The implant is placed in a disposable polypropylene flat base tube (sarstedt No 58.537 with No 65.790 cap) and 30 mL PBS is added. The tubes are placed in 39° C. Fisher Shaking Water with (Model 129-shaker setting at 2¾).

The PBs is changed daily and samples are assayed for peptide released by counting using the scintillation counter. During the course of the experiment some of the samples had to be diluted 1 to 10 with PBs before counting.

VI. Results and Discussion

Table IV summarizes the steer labeled tristearate data in vitro and in vivo. In the in vitro release profile, the implant released 1.6–2.5 mg/day after the initial burst until the pGLA (copoly-L-lactide/glycolide) coating started to lose integrity after three weeks. The in vivo release system, calculated from the daily excretion of radiolabeled material, is similar to the in vitro profile. The in vivo implant released an average of 3.2 mg/day over the 43 day experiment. The peptide is found at an increasing level in the steer's blood over time.

TABLE IV

| | | | Steer/Tristearate Data In Vivo | | | | Daily Waste | | |
|---|---|---|---|---|---|---|---|---|---|
| | In Vitro | | Urine | Feces | Total | Total | mL | kg | Blood Level |
| Day | mg/day | Cum % | mg/day | mg/day | mg/day | Cum % | Urine | Feces | mg/steer |
| 1 | 3.70 | 1.9 | 0.43 | 4.50 | 4.93 | 2.8 | 1800.0 | 3.0 | 0.154 |
| 2 | 2.10 | 3.0 | 0.53 | 6.80 | 7.33 | 5.9 | 3460.0 | 7.0 | 0.159 |
| 3 | 2.01 | 4.0 | 0.35 | 2.40 | 2.75 | 7.6 | 3310.0 | 9.9 | 0.146 |
| 4 | 2.70 | 5.4 | 0.28 | 1.98 | 2.26 | 8.8 | 3250.0 | 11.9 | — |
| 5 | 1.65 | 6.2 | 0.25 | 2.30 | 2.55 | 10.2 | 3260.0 | 9.8 | — |
| 6 | 1.65 | 7.1 | 0.28 | 1.47 | 1.75 | 11.2 | 3920.0 | 7.4 | 0.163 |
| 7 | 1.60 | 7.9 | 0.27 | 1.57 | 1.84 | 12.3 | 4020.0 | 9.7 | 0.41 |
| 8 | 1.60 | 8.7 | 0.30 | 2.24 | 2.54 | 13.7 | 3000.0 | 8.8 | — |
| 9 | 1.55 | 9.5 | 0.32 | 1.78 | 2.10 | 14.9 | 3050.0 | 5.0 | — |
| 10 | 1.68 | 10.4 | 0.35 | 2.44 | 2.79 | 16.5 | 2400.0 | 5.2 | 0.305 |
| 11 | 1.71 | 11.3 | 0.32 | 1.72 | 2.04 | 17.7 | 2650.0 | 11.0 | — |
| 12 | 1.71 | 12.1 | 0.24 | 1.92 | 2.16 | 19.0 | 2640.0 | 8.9 | — |
| 13 | 1.71 | 13.0 | 0.31 | 2.29 | 2.60 | 20.5 | 3510.0 | 9.2 | 0.279 |
| 14 | 2.26 | 14.2 | 0.26 | 1.58 | 1.84 | 21.6 | 3090.0 | 7.2 | — |
| 15 | 1.56 | 15.0 | 0.30 | 1.84 | 2.14 | 22.8 | 2930.0 | 8.0 | 0.349 |
| 16 | 2.60 | 16.3 | 0.32 | 1.65 | 1.97 | 23.9 | 3340.0 | 8.9 | — |
| 17 | 2.14 | 17.4 | 0.43 | 3.45 | 3.88 | 26.1 | 4000.0 | 11.4 | 0.289 |
| 18 | 2.16 | 18.5 | 0.39 | 2.57 | 3.00 | 2.78 | 4040.0 | 7.4 | — |
| 19 | 2.16 | 19.6 | 0.52 | 4.12 | 4.64 | 30.5 | 4340.0 | 7.4 | — |
| 20 | 2.16 | 20.7 | 0.48 | 2.57 | 3.05 | 33.7 | 3540.0 | 5.4 | 0.388 |
| 21 | 5.57 | 23.6 | 0.59 | 4.16 | 4.75 | 36.4 | 4540.0 | 9.6 | — |
| 22 | 5.90 | 26.6 | 0.52 | 2.11 | 2.63 | 37.9 | 4040.0 | 4.2 | 0.471 |
| 23 | 5.87 | 29.6 | 0.67 | 3.21 | 3.88 | 40.2 | 2980.0 | 5.6 | — |
| 24 | 6.01 | 32.7 | 0.62 | 4.17 | 4.80 | 43.0 | 2620.0 | 10.8 | 0.513 |
| 25 | 5.16 | 35.4 | 0.52 | 6.12 | 6.64 | 46.8 | 2929.0 | 8.8 | — |
| 26 | 5.16 | 38.0 | 0.54 | 4.33 | 4.87 | 49.6 | 3400.0 | 10.5 | — |
| 27 | 5.16 | 40.7 | 0.72 | 4.23 | 4.95 | 52.4 | 3440.0 | 9.8 | 0.584 |

TABLE IV-continued

| | | | Steer/Tristearate Data | | | | | | |
|---|---|---|---|---|---|---|---|---|---|
| | | | | In Vivo | | | Daily Waste | | |
| | In Vitro | | Urine | Feces | Total | Total | mL | kg | Blood Level |
| Day | mg/day | Cum % | mg/day | mg/day | mg/day | Cum % | Urine | Feces | mg/steer |
| 28 | 6.28 | 43.9 | 0.90 | 8.20 | 9.10 | 57.6 | 4140.0 | 8.6 | — |
| 29 | 5.31 | 46.6 | 0.67 | 5.57 | 6.24 | 61.2 | 3560.0 | 5.6 | — |
| 30 | 4.16 | 48.8 | 0.55 | 3.37 | 3.90 | 63.5 | 3040.0 | 7.9 | — |
| 31 | 4.22 | 50.9 | 0.45 | 4.05 | 4.50 | 66.1 | 3540.0 | 12.8 | 0.790 |
| 32 | 3.20 | 52.6 | 0.38 | 3.56 | 3.94 | 68.3 | 4740.0 | 9.2 | — |
| 33 | 3.20 | 54.2 | 0.36 | 3.49 | 3.85 | 70.5 | 4500.0 | 9.3 | — |
| 34 | 2.90 | 55.7 | 0.36 | 2.52 | 2.88 | 72.2 | 4320.0 | 3.8 | — |
| 35 | 2.90 | 57.2 | 0.35 | 2.28 | 2.63 | 73.7 | 3660.0 | 6.2 | — |
| 36 | 3.80 | 59.2 | 0.31 | 1.61 | 1.92 | 75.2 | 3000.0 | 6.2 | 0.800 |
| 37 | 3.74 | 61.1 | 0.22 | 1.46 | 1.68 | 76.1 | 2920.0 | 6.3 | — |
| 38 | 3.86 | 63.0 | 0.17 | 0.40 | 0.57 | 76.5 | 1040.0 | 3.4 | 0.700 |
| 39 | 2.01 | 64.1 | 0.84 | 0.90 | 1.74 | 77.5 | 3640.0 | 5.1 | — |
| 40 | 2.01 | 65.1 | 0.09 | 0.85 | 0.94 | 78.0 | 1360.0 | 8.8 | — |
| 41 | 2.01 | 66.1 | 0.14 | 0.54 | 0.68 | 78.4 | 3440.0 | 9.2 | 0.720 |
| 42 | 3.06 | 67.7 | 0.09 | 0.10 | 0.19 | 78.5 | 2480.0 | 6.5 | — |
| 43 | 2.70 | 69.1 | 0.04 | 0.18 | 0.22 | 78.6 | 440.0 | 2.3 | 0.740 |
| | | 1.6 per day | | | | 1.8 per day | | | |

EXAMPLES 23-27

The laurate salt of bradykinin, the stearate salt of a growth releasing factor (D-ala2-GRF 1-29, the stearate salt of luteinizing hormone releasing hormone, the stearate salt of polylysine were prepared; pressed into implants; coated; selectively partially uncoated; and the in vitro dissolution release profiles established according to the methods described in the subject case. For comparison, implants were prepared the amount of drug released was calculated for the dissolution rates of uncoated peptides, partially coated peptides and uncoated fatty acid salts of the peptides.

The structures of these peptides are:

Bradykinin

Arg-Pro-Gly-Phe-Ser-Pro-Phe-Arg

Luteinizing Hormone Releasing Hormone (LLHRH)

pGlu-His-Trp-Ser-Try-Gly-Leu-Agr-Pro-Gly-NH₂

Poly-L-Lysine(Molecular weight avg 3700)

Growth Releasing Factor (GRF)

Tyr—D—Ala—Asp—Ala—Ile—Phe—Thr—Asn—Ser—Tyr—Agr—Lys—Val—Leu—Gly—Gln—Leu—Ser—Ala—Arg—Lys—Leu—Leu—Gln—Asp—Ile—Met—Ser—Arg—NH₂

The salts were prepared as follows:

Materials For The Preparation of Fatty Acid Salts

Stearic acid: Aldrich, 99+%, No. 26,830.
Lauric acid: Aldrich, 99.5+%, No. 15,378.
Piperidine: Aldrich, 99% No. 10,409-4.

Preparation of Polylysine Stearate

Stearic acid (6.0 g, 21 mmol) was dissolved in 200 mL of methanol in a round bottom flask by warming in a 35°-40° C. water bath; 400 mg (1.9 mmol monomer units) of poly-L-lysine (Sigma p-0879, avg. MW 3700, hydrobromide salt) was dissolved in 10 mL methanol, and 275 mg (3.22 mmol) of piperidine was added. The peptide solution was then added to the stearic acid solution and stirred for three to four hours. The solvent was evaporated by rotary evaporation; 250 mL of ether/chloroform (6:4) was to the residue, and stirred for one hour. The mixture was filtered through a 5 μm teflon filter (Millipore Type LS), and the solid product (421 mg) collected and dried in a vacuum dessicator. The NMR (methanol d-4) confirmed the presence of stearate at 1.3-1.4 ppm.

Preparation of Bradykinin Laurate

Lauric acid (2 g, 10 mmol) was dissolved in 80 mL of methanol in a round bottom flask; 160 mg (0.13 mmol) of bradykinin was dissolved in 10 mL methanol, and 112 mg (1.36 mmol) of piperidine was. The peptide solution was then added to the stearic acid solution and stirred for three to four hours. The solvent was evaporated by rotary evaporation; 150 mL of ether/chloroform (6:4) was added to the residue, and stirred for one hour. The mixture was filtered through a 5 μm teflon filter (Millipore Type Ls), and the solid product (85 mg) collected and dried in a vacuum dessicator. The NMR (methanol d-4) confirmed the presence of laurate at 1.3-1.4 ppm.

Preparation of LHRH Stearate

Stearic acid (1.4 g, 4.9 mmol) was dissolved in 50 mL of methanol in a round bottom flask by warming in a 35°-40° C. water mg (0.06 mmol) of LHRH (Luteinizing Hormone Releasing Hormone, Sigma L-1743, acetate salt) was dissolved in 10 mL methanol, and 35 mg (0.41 mmol) of piperidine was added. The peptide solution was then added to the stearic acid solution and stirred for three to four hours. The solvent was evaporated by rotary evaporation; 100 mL of ether/chloroform (6:4) was added to the residue, and stirred for one hour. The mixture was filtered through a 5 μm teflon filter (Millipore Type LS), and the solid product (70 μg) collected and dried in a vacuum dessicator. The NMR (methanol d-4) confirmed the presence of stearate at 1.3-1.4 ppm.

Preparation of GRF Stearate

Stearic acid (1.5 g, 5.3 mmol) was dissolved in 50 mL of methanol in a round bottom flask by warming in an 35°-40° C. water bath; 115 mg (0.035 mmol) of growth Hormone Releasing Factor (D-Ala2-GRF 1-29, Cynamid Lot DC-21-106) was dissolved in 10 mL methanol, and 60 mg (0.70 mmol) of piperidine was added. The peptide solution was then added to the stearic acid solution and stirred for three to four hours. The solvent was evaporated by rotary evaporation; 80 mL of ether/chloroform (8:2) was added to the residue, and stirred for one hour. The mixture was filtered through a 5 μm teflon filter (Millipore Type LS), and the solid product (112 mg) collected and dried in a vacuum dessicator. The NMR (methanol d-4) confirmed the presence of stearate at 1.3-1.4 ppm.

Preparation of Implant

Cylindrical implants (⅛" diameter) were made with a custom mold by pressing in an Carver Press at ≦1000 pounds pressure for a few seconds at room temperature. The weight of the implants ranged from 22 mg to 52 mg. Depending on the material, the implants measured 9.1 mg/mm to 10.3 mg/mm in weight/length. Certain implants Were left uncoated for comparative purposes. Other implants were coated with silastic medical adhesive type A by dip coating the implants from a 35% dispersion of pf adhesive A in hexane. These implants were cured overnight at room temperature. Later, the two base ends of each implant were opened by carefully removing the coating with a razor. Thus, release could occur from only these two decoated surfaces. The coating weighed 1-3% of the implant weight.

In vitro Dissolution

Each of the implants was placed in a plastic tube in contact with known amounts (10 or 30 mL) of phosphate buffered saline (pH 7.1). The tubes were placed in a gently shaking water bath at 39° C. After definite time periods, the buffer was removed and analyzed for drug released by Uv measurement at 220 nm. The buffer was replaced at each timepoint. The amount of drug released was calculated by concentration-absorbance relationships which were established prior to the in vitro dissolution experiments. Known concentrations of the peptide salt solutions were measured to establish these relationships.

| In vitro Dissolution of Bradykinin Implants | | |
|---|---|---|
| | Cumulative & Released | |
| Days | Bradykinin Uncoated | Bradykinin Laurate Coated |
| 1 | 80.3 | 46.2 |
| 2 | 100 | 64.6 |
| 3 | — | 76.5 |
| 6 | — | 81.0 |
| 13 | — | 85.1 |

| In Vitro Dissolution of GRF Implants | | | |
|---|---|---|---|
| | Cumulative & Released | | |
| Days | GRF Uncoated | GRF Stearate Uncoated | GRF Stearate Coated |
| 1 | 100 | 28.9 | 12.5 |
| 2 | — | 47.6 | 21.3 |
| 3 | — | 62.2 | 28.0 |
| 6 | — | 88.9 | 37.1 |
| 13 | — | 100 | 40.0 |

| In vitro Dissolution Profiles: | | | |
|---|---|---|---|
| | Cumulative & Released | | |
| Days | Polylysine Uncoated | Polylysine Coated | Polylysine Stearate Salt Uncoated | Polylysine Stearate Salt Coated |
| 1 | 100 | 100 | 75.4 | 32.1 |
| 2 | — | — | 78.0 | 34.7 |
| 3 | — | — | 78.5 | 35.8 |
| 6 | — | — | 80.0 | 36.4 |
| 13 | — | — | 83.0 | 38.5 |
| 20 | — | — | 83.1 | 39.4 |
| 31 | — | — | 84.2 | 40.6 |
| 41 | — | — | 92.0 | 45.3 |

The dissolution kinetics and rate are altered by making the stearate salt of polylysine and by further coating the cylindrical implant and having the ends exposed. Complete dissolution has not occurred for these implants after 41 days. In contrast, the uncoated and partially coated polylysine implants were totally dissolved in the media after only one hour. The sole material remaining in the buffer was a thin piece of silastic coating.

| In vitro Dissolution of LHRH Implants | | | |
|---|---|---|---|
| | Cumulative & Released | | |
| Days | LHRH Uncoated | LHRH Coated | LHRH Stearate Uncoated | LHRH Stearate Coated |
| 1 | 100 | 100 | 100 | 67.5 |
| 2 | — | — | — | 95.7 |
| 3 | — | — | — | 96.6 |
| 6 | — | — | — | 96.7 |
| 13 | — | — | — | 97.0 |

The examples illustrate that the partially coated, fatty acid salts of bradykinin, luteinizing hormone releasing hormone, growth releasing factor and poly-1-lysine release an essentially uniform and continuous amount of the peptides over an extended period of time.

What is claimed is:

1. A composition for the parenteral administration of an essentially uniform and continuous amount of a peptide, having a molecular weight of up to about 5,000, over an extended period of time which comprises a compacted and partially coated $C_{10}$–$C_{20}$ fatty acid salt of the peptide, which exhibits some degree of solubility in an aqueous physiological environment.

2. A composition according to claim 1, wherein the coating is biodegradable or non-biodegradable.

3. A composition according to claim 1, wherein the peptide is selected from the group consisting of his-D-trp-ala-trp-D-phe-lys-NH$_2$, bradykinin, luteinizing hormone releasing hormone, growth releasing factor and poly-1-lysine.

4. A composition according to claim 1, wherein the salt is tristearate.

5. A method for adjusting parenterally an essentially uniform and continuous amount of a peptide, having a molecular weight of up to about 5,000, over an extended period of time which comprises implanted a compacted and partially coated $C_{10}$–$C_{20}$ fatty acid salt of the peptide, which exhibits some degree of solubility in an aqueous physiological environment.

6. A composition according to claim 5, wherein the coating is biodegradable or non-biodegradable.

7. A composition according to claim 5, wherein the peptide is selected from the group consisting of his-D-trp-ala-trp-D-phe-lys-NH$_2$, bradykinin, luteinizing hormone releasing hormone, growth releasing factor and poly-1-lysine.

8. A composition according to claim 5, wherein the salt is tristearate.

9. A method for preparing an implant for the parenteral administration of an essentially uniform and continuous amount of a peptide, having a molecular weight of up to about 5,000, over an extended period of time which comprises compacting a $C_{10}$–$C_{20}$ fatty acid salt of the peptide, which exhibits some degree of solubility in an aqueous physiological environment, into the form of an implant; coating the implant with a coating material; and removing a section of the coating material from the coated implant to expose the peptide.

10. A composition according to claim 9, wherein the coating is biodegradable or non-biodegradable.

11. A composition according to claim 9, wherein the peptide is selected from the group consisting of his-D-trp-ala-trp-D-phe-lys-NH$_2$, bradykinin, luteinizing hormone releasing hormone, growth releasing factor and poly-1-lysine.

12. A composition according to claim 9, wherein the salt is tristearate.

* * * * *

UNITED STATES PATENT AND TRADEMARK OFFICE
CERTIFICATE OF CORRECTION

PATENT NO. : 5,137,874

DATED : August 11, 1992

INVENTOR(S) : Susan M. Cady; Richard Fishbein

It is certified that error appears in the above-indentified patent and that said Letters Patent is hereby corrected as shown below:

Column 13, claim 5, line 8, "implanted" should read —implanting—.

Column 13, claim 6, line 12, claim 7, line 14, claim 8, line 21, claim 10, line 11, claim 11, line 13, and claim 12, line 20, "composition", each occurrence, should read —method—.

Signed and Sealed this

Fourth Day of October, 1994

Attest:

BRUCE LEHMAN

*Attesting Officer*    *Commissioner of Patents and Trademarks*